(12) United States Patent
Svanberg et al.

(10) Patent No.: US 12,178,548 B2
(45) Date of Patent: Dec. 31, 2024

(54) SYSTEM AND METHOD FOR LASER BASED INTERNAL ANALYSIS OF GASES IN A BODY OF A HUMAN

(71) Applicant: NEOLA MEDICAL AB, Lund (SE)

(72) Inventors: Sune Svanberg, Lund (SE); Emilie Krite Svanberg, Lund (SE); Marcus Larsson, Bjarred (SE)

(73) Assignee: NEOLA MEDICAL AB, Lund (SE)

( * ) Notice: Subject to any disclaimer, the term of this patent is extended or adjusted under 35 U.S.C. 154(b) by 0 days.

(21) Appl. No.: 18/224,882

(22) Filed: Jul. 21, 2023

(65) Prior Publication Data

US 2023/0380693 A1  Nov. 30, 2023

Related U.S. Application Data

(63) Continuation of application No. 15/752,823, filed as application No. PCT/EP2016/069549 on Aug. 17, 2016, now Pat. No. 11,744,467.

(30) Foreign Application Priority Data

Aug. 17, 2015 (SE) .................................. 1500335-3

(51) Int. Cl.
*A61B 5/00* (2006.01)
*A61B 1/00* (2006.01)
(Continued)

(52) U.S. Cl.
CPC ........ *A61B 5/0084* (2013.01); *A61B 1/00013* (2013.01); *A61B 1/00165* (2013.01);
(Continued)

(58) Field of Classification Search
CPC .............. A61B 5/0084; A61B 1/00013; A61B 1/00165; A61B 1/063; A61B 1/07;
(Continued)

(56) References Cited

U.S. PATENT DOCUMENTS

| 5,019,040 A | 5/1991 | Itaoka et al. |
| 6,567,165 B1 | 5/2003 | Tsuchiya et al. |

(Continued)

FOREIGN PATENT DOCUMENTS

| CN | 102088896 A | 6/2011 |
| CN | 102401914 A | 4/2012 |

(Continued)

OTHER PUBLICATIONS

Translation of Decision of Rejection dated Jan. 12, 2021, in connection with Chinese Patent Application No. 201680047796.3.

(Continued)

*Primary Examiner* — Ryan D Walsh
(74) *Attorney, Agent, or Firm* — Norris McLaughlin, P.A.

(57) ABSTRACT

A device, system and method for measuring free gas in a cavity of a subject. The device, system and method include a light source for emitting light with a wavelength associated with an absorption band of the free gas, an optical fibre connected to the light source and adapted to be inserted using an introducing member for internal illumination, and a detector adapted to be positioned on a skin surface for detecting light transmitted through the tissue. The device, system and method further includes a control unit for evaluating the detected transmitted light for determining the free gas, or a distribution of the free gas, or concentration of the free gas.

13 Claims, 4 Drawing Sheets

(51) Int. Cl.

| | | |
|---|---|---|
| *A61B 1/06* | (2006.01) | |
| *A61B 1/07* | (2006.01) | |
| *A61B 1/267* | (2006.01) | |
| *A61B 1/273* | (2006.01) | |
| *A61B 1/31* | (2006.01) | |
| *A61B 5/08* | (2006.01) | |
| *A61B 90/00* | (2016.01) | |
| *A61M 16/00* | (2006.01) | |
| *G01J 3/42* | (2006.01) | |
| *G01N 21/49* | (2006.01) | |

(52) U.S. Cl.
CPC ............... *A61B 1/063* (2013.01); *A61B 1/07* (2013.01); *A61B 1/267* (2013.01); *A61B 1/2676* (2013.01); *A61B 1/2733* (2013.01); *A61B 1/31* (2013.01); *A61B 5/0059* (2013.01); *A61B 5/0075* (2013.01); *A61B 5/08* (2013.01); *A61B 5/4839* (2013.01); *A61B 5/6853* (2013.01); *A61B 5/746* (2013.01); *A61M 16/024* (2017.08); *G01J 3/42* (2013.01); *G01N 21/49* (2013.01); *A61B 1/00* (2013.01); *A61B 1/0661* (2013.01); *A61B 2090/3618* (2016.02); *A61B 2562/0238* (2013.01)

(58) Field of Classification Search
CPC ..... A61B 1/267; A61B 1/2676; A61B 1/2733; A61B 1/31; A61B 5/0059; A61B 5/0075; A61B 5/08; A61B 5/4839; A61B 5/6853; A61B 5/746; A61B 1/00; A61B 1/0661; A61B 2090/3618; A61B 2562/0238; A61M 16/024; G01J 3/42; G01N 21/49
See application file for complete search history.

(56) References Cited

U.S. PATENT DOCUMENTS

| | | |
|---|---|---|
| 8,849,079 B2 | 9/2014 | Yoshida et al. |
| 11,744,467 B2 * | 9/2023 | Svanberg ............. A61B 5/0075 600/478 |
| 2005/0148092 A1 | 7/2005 | Svanberg et al. |
| 2009/0118646 A1 | 5/2009 | Svanberg et al. |
| 2010/0186742 A1 | 7/2010 | Sherman et al. |
| 2011/0009772 A1 | 1/2011 | Braun et al. |
| 2012/0051693 A1 | 3/2012 | Yoshida et al. |
| 2012/0140229 A1 | 6/2012 | Svanberg et al. |
| 2014/0039256 A1 | 2/2014 | Gavriely |
| 2014/0046142 A1 | 2/2014 | Gavriely et al. |
| 2015/0190649 A1 | 7/2015 | Gelfand et al. |
| 2015/0201870 A1 | 7/2015 | Gelbart |
| 2015/0223698 A1 | 8/2015 | Subramaniam et al. |
| 2016/0174887 A1 | 6/2016 | Kirenko |
| 2022/0202311 A1 | 6/2022 | Fellman et al. |

FOREIGN PATENT DOCUMENTS

| | | |
|---|---|---|
| CN | 103393439 A | 11/2013 |
| CN | 204260838 U | 4/2015 |
| EP | 0628804 A1 | 12/1994 |
| EP | 0760477 A2 | 3/1997 |
| EP | 0826958 A2 | 3/1998 |
| SE | 530817 C2 | 9/2008 |
| SE | 1100406 A1 | 11/2012 |
| WO | 03/078983 A1 | 9/2003 |
| WO | 2006/112789 A1 | 10/2006 |
| WO | 2007/088215 A1 | 8/2007 |
| WO | 2018/104888 A1 | 6/2018 |
| WO | 2020/216839 A1 | 10/2020 |

OTHER PUBLICATIONS

International Search Report for corresponding application PCT/EP2016/069549 dated Nov. 3, 2016.
Written Opinion of the International Searching Authority for corresponding application PCT/EP2016/069549 dated Nov. 3, 2016.
L. Persson, et al., "Gas Monitoring in Human Sinuses Using Tunable Diode Laser Spectroscopy", Journal of Biomedical Optics, vol. 12, No. 5, Jan. 1, 2007, pp. 054001-1,-8 XP055015485.
P. Lundin, et al., "Non-invasive gas monitoring in newborn infants using diode laser absorbtion spectroscopy: a case study", Optical Diagnostics and Sensing X11: Toward Point-of-Care Diagnostics; and Design and Performance Validation if Phantoms used in Conjunction with Optical Measurement of Tissue IV; SPIE, Bellingham, Washington, USA, vol. 8229, No. 1, Feb. 9, 2012, pp. 1-11, XP060002108.
D. A. Boas, et al., "Imaging the Body with Diffuse Optical Tomography", IEEE Signal Processing Magazine, IEEE Service Center, Piscataway, NJ, US, vol. 8, No. 6, Nov. 1, 2001, pp. 57-75, XP011092366, ISSN: 1053-5888.
S.A. Switzerland: "Medlight Diffusing balloon catheter Model CBD", Jan. 1, 2008, XP055313569, retrieved from the Internet: URL:http://www.medlight.com/pdf/Doc_CDB_0801E.pdf on Oct. 25, 2016, pp. 1-2.
English Translation of Chinese Office Action dated Jun. 23, 2020, in connection with Chinese Patent Application No. 201680047796.3.
Office Action dated Oct. 30, 2020, in connection with European Patent Application No. 16753905.5.
European Search Report dated Feb. 10, 2023, in connection with European Patent Application No. 22 18 8415.8.
European Extended Search and Opinion dated Feb. 17, 2023, in connection with European Application No. 22 18 8415.8.
Swedish Office Action for corresponding application SE 1500335-3 dated Feb. 16, 2016.

* cited by examiner

SYSTEM AND METHOD FOR LASER BASED INTERNAL ANALYSIS OF GASES IN A BODY OF A HUMAN

This application is a continuation of U.S. application Ser. No. 15/752,823, filed Feb. 14, 2018, which is § 371 U.S. National stage of PCT International Patent Application No. PCT/EP2016/069549, filed Aug. 17, 2016, which claims foreign priority benefit of Swedish Patent Application No. SE 1500335-3, filed Aug. 17, 2015, the disclosures of each of which patent applications are incorporated herein by reference.

BACKGROUND OF THE INVENTION

Field of the Invention

This disclosure pertains to analysis of gases in a body of a human, by positioning a light source, such as a fibre connected to a laser, inside a cavity of the body. Especially, the disclosure relates to positioning the light source in the trachea, or in the digestive system, such as in the oesophagus or the intestines, for performing measurements on physiological gases.

Description of the Prior Art

Physiological gases, such as, oxygen, nitrogen, nitric oxide (NO), carbon dioxide, and water vapour exist inside many cavities in the human body, for example, lungs, sinuses, and the middle ear. The digestive system is a further location for gases. Oxygen in the lungs is of special interest as it is a prerequisite for vital functions of a human. Monitoring oxygen in the lungs is of interest, particularly, for premature new-born infants. In connection with the diseases in the cavities of the head, for example, sinusitis or otitis media, the gas filled cavity may be filled with liquids and the gas signal will decrease or disappear.

Substances may be identified with optical spectroscopy by utilizing characteristic absorption signals. While the spectroscopic signals from liquids and solids are relatively broad, typically 10's of nanometers, free gases are characterized by absorption lines being about 10000 times sharper, typically around 0.001 nm. This difference in the absorption signal makes it possible to detect free gases in cavities or pores enclosed by condensed material, such as human tissue. This is the fundamental principle for the technology called GASMAS (Gas in Scattering Media Absorption Spectroscopy) technology, S. Svanberg, Gas in Scattering Media Absorption Spectroscopy—from Basic Studies to Biomedical Applications, Lasers and Photonics Reviews 7, 779 (2013).

The GASMAS technology has been used for characterizing sinuses and middle ear, for example in S. Svanberg, L. Persson and K. Svanberg, Human cavity gas measurement method and device; Swedish Patent Application 0500878-4; L. Persson, M. Andersson, M. Cassel-Engquist, K. Svanberg and S. Svanberg, Gas Monitoring in Human Sinuses using Tunable Diode Laser Spectroscopy, J. Biomed. Optics 12, 2028 (2007); L. Persson, M. Lewander, M. Andersson, K. Svanberg and S. Svanberg, Simultaneous Detection of Molecular Oxygen and Water Vapor in the Tissue Optical Window using Tunable Diode Laser Spectroscopy, Applied Optics 47, 2028 (2008); M. Lewander, Z. G. Guan, K. Svanberg, S. Svanberg and T. Svensson, Clinical System for Non-invasive in situ Monitoring of Gases in the Human Paranasal Sinuses, Optics Express 13, 10849 (2009); M. Lewander, S. Lindberg, T. Svensson, R. Siemund, K. Svanberg, S. Svanberg, Clinical Study Assessing Information on the Maxillary and Frontal Sinuses using Diode Laser Gas Spectroscopy, Rhinology 50, 26 (2011); J. Huang, H. Zhang, T. Q. Li, H. Y. Lin, K. Svanberg, and S. Svanberg, Assessment of Human Sinus Cavity Air Volume using Tunable Diode Laser Spectroscopy, with Application to Sinusitis Diagnostics, J. Biophotonic DOI 10.1002/jbio.201500110; K. Svanberg and S. Svanberg, Monitoring of Free Gas In-Situ for Medical Diagnostics using Laser Spectroscopic Techniques, in Frontiers in Biophotonics for Translational Medicine, U.S. Dimish and M. Olivo (eds) (Springer, Singapore 2015) 307-321; H. Zhang, J. Huang, T. Q. Li, S. Svanberg, and K. Svanberg, Optical Detection of Middle Ear Infection using Spectroscopic Techniques—Phantom Experiments, J. Biomedical Optics 20, 057001 (2015). The GASMAS technology has also been used in studies for characterization of gases in lungs and intestines in full-term newborn infants, P. Lundin, E. Krite Svanberg, L. Cocola, M. Lewander Xu, G. Somesfalean, S. Andersson-Engels, J. Jahr, V. Fellman, K. Svanberg, and S. Svanberg, Non-invasive Monitoring of Gas in the Lungs and Intestines of Newborn Infants using Diode Lasers: Feasibility Study, J. Biomedical Optics 18, 127005 (2013); E. Krite Svanberg, P. Lundin, M. Larsson, J. Akeson, K. Svanberg, S. Svanberg, S. Andersson-Engels and V. Fellman, Non-invasive monitoring of oxygen in the lungs of Newborn Infants Using Diode Laser Spectroscopy, Pediatrics Research, 79, 621 (2015).

Both oxygen and water vapour may be registered in most of the cases, but not always. The reason a signal was not detected may be due to the low signal strength after the detected light had passed a long path through the enclosing tissue.

Hence, new improved apparatus and methods for detecting free gases inside cavities of the human body are advantageous.

SUMMARY OF THE DISCLOSURE

Accordingly, embodiments of the present disclosure preferably seek to mitigate, alleviate or eliminate one or more deficiencies, disadvantages or issues in the art, such as the above-identified, singly or in any combination by providing a device, system or method according to the description for measuring free gas in a cavity, such as a lung or in the digestive system.

In accordance to a first aspect, a device for measuring free gas in a cavity of a subject is disclosed. The device comprises a light source for emitting light with a wavelength associated with an absorption band of the free gas; an optical fibre connected to the light source and adapted to be inserted internally in the subject using an introducing member; a detector unit adapted to be positioned on a skin surface for detecting light transmitted through tissue of the subject. The device further comprises a control unit for evaluating the detected transmitted light for determining a concentration of the free gas or a distribution of the free gas.

In some examples of the disclosure, the control unit of the device may be configured for detecting the free gas in the cavity.

In some examples of the disclosure, the light source of the device may be a laser.

In some examples of the disclosure, the device may comprise at least two light sources having different wavelengths.

Additionally, in some examples of the disclosure, at least one light source of the at least two light sources may have a wavelength associated with an absorption band of a reference gas.

In some examples of the disclosure the reference gas may be water vapour.

In some examples of the disclosure may the free gas be a physiological gas or a mixture of gases.

In some examples of the disclosure the physiological gas may be any of oxygen, nitric oxide (NO), carbon dioxide, and water vapour.

In some examples of the disclosure the optical fibre may include a light diffusor at an end of the optical fibre adapted to be position in an introducing member.

In some examples of the disclosure the control unit may be configured for controlling a medical ventilator based on the distribution of the free gas, or the concentration of the free gas.

In some examples of the disclosure the control unit may be configured for controlling an administration of a medicament based the distribution of the free gas, or the concentration of the free gas.

In some examples of the disclosure the control unit may be configured for activating an alarm when the determined the free gas, or the distribution of the free gas, or the concentration of the free gas reaches or passes a selected threshold value.

In some examples of the disclosure the distribution of the free gas, or the concentration of the free gas may be used for determining a lung functioning of the subject. In some examples of the disclosure the light may be emitted from more than one location, and the transmitted light may be detected by more than one detector unit.

In some examples of the disclosure diffuse optical tomography may be used for evaluating the distribution of the free gas.

In some examples of the disclosure the evaluation may be obtained as a three-dimensional gas distribution.

In some examples of the disclosure the detector unit may be an imaging sensor configured, and the light source sequentially emitting an absorbing wavelength and a close non-absorbing wavelength, and the image sensor detecting two images which may then be compared by the control unit.

In some examples of the disclosure the control unit may evaluate line profile changes in an absorption spectrum for determining the concentration of the free gas or the distribution of the free gas.

In a further aspect, a system for measuring free gas in a cavity of a subject is disclosed. The system comprises an introducing member to be arranged in a channel or duct of the subject; a light source for emitting light with a wavelength associated with an absorption band of the free gas; an optical fibre connected to the light source and adapted to be inserted into the introducing member; and a detector unit adapted to be positioned on a skin surface for detecting light transmitted through tissue of the subject. The system may further include a control unit for evaluating the detected transmitted light for determining the concentration of the free gas or the distribution of the free gas.

In some examples of the disclosure the introducing member may be either: a tracheal tube, an endotracheal tube, a bronchoscope, an endoscope, or a colonoscope.

In some examples of the disclosure the introducing member may be a nasogastric feeding tube adapted to be inserted into the oesophagus.

In some examples of the disclosure the introducing member may have an expandable balloon or cuff.

In some examples of the disclosure the expandable balloon of cuff may be made from a light diffusing material.

In some examples of the disclosure the inner walls of the expandable balloon of cuff may have a light reflecting coating.

In some examples of the disclosure the expandable balloon of cuff may be arranged at an end section of the introducing member.

In some examples of the disclosure an end section of the introducing member may be coupled to the optical fibre.

In some examples of the disclosure the optical fibre may be embedded into a wall of the introducing member.

In a further aspect, a method of measuring free gas in a cavity of a subject is disclosed. The method comprising the steps of arranging an introducing member in a channel of the subject;
  positioning an optical fibre connected to a light source in introducing member;
  positioning a detector unit on a skin surface;
  emitting light using the light source, the emitted light having a wavelength associated with an absorption band of the free gas;
  detecting light transmitted through the tissue by the detector unit; and
  evaluating the detected transmitted light using a control unit for determining the concentration of the free gas or a distribution of the free gas.

In some examples of the disclosure may the detector at positioned at the chest of the subject.

In some examples of the disclosure the channel may be a trachea or an oesophagus.

In some examples of the disclosure the detector may be positioned at the abdomen of the subject.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EXAMPLES

Figure 1:
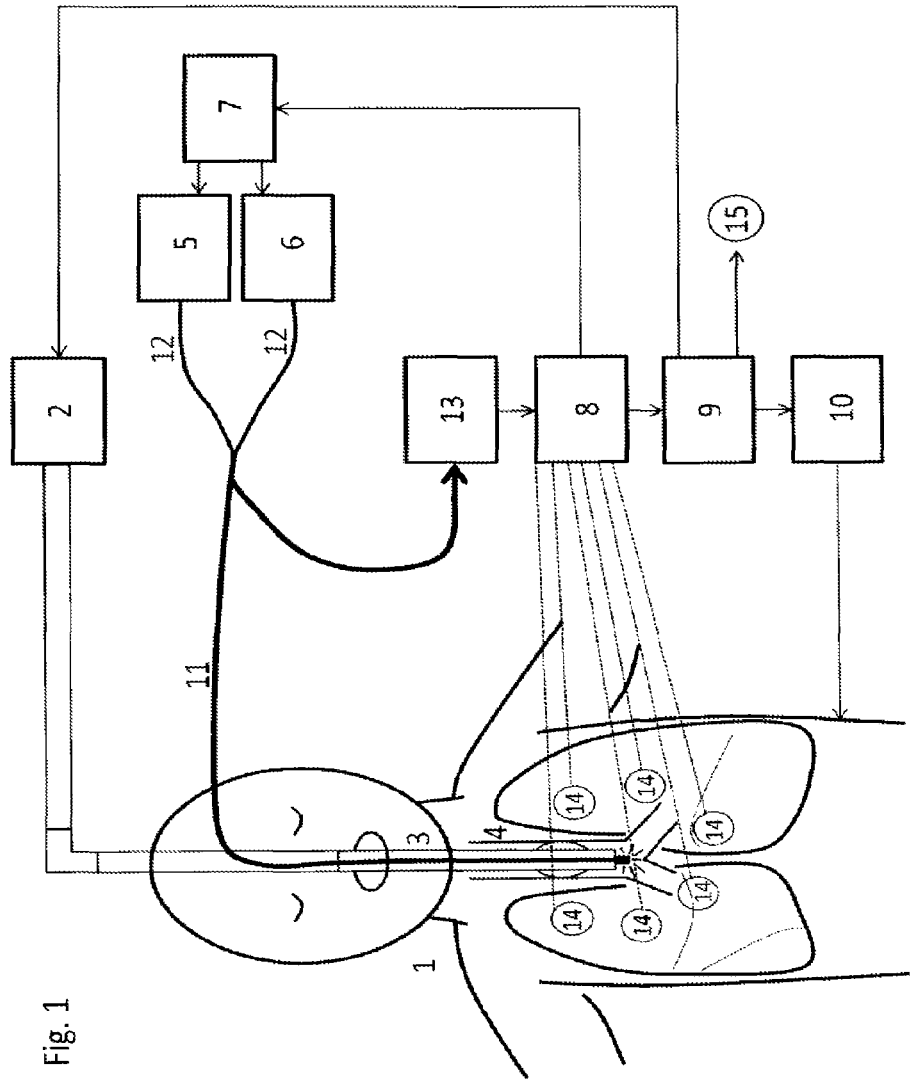
FIG. 1 is illustrating an example of a disclosed device and system.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art.

The following disclosure focuses on examples of the present disclosure applicable to analyse or monitoring free physiological gases in human cavities by arranging a light source in a cavity, such as in the trachea, or in the digestive system, such as in the oesophagus or the intestines, such as parts of the digestive tract and detecting the transmitted light using one or a plurality of detectors arranged outside the human body.

For example, this is advantageous for detecting weak signals due to the light passing a long path through the tissue enclosing the cavity.

When monitoring gases using narrow-band light, such as laser light, the light has been transmitted towards the skin over the cavity containing the free gas, such as the lungs or intestines. The light that has penetrated enough tissue to reach the cavity is scattered and transmitted to a detector positioned against the skin a few centimetres laterally the light source. Thereby is a non-invasive measurement procedure performed but the light transmitted from the light source that reaches the detector will be heavily attenuated by the tissue the light has to pass between the light source and the detector and the scattered light will then be further attenuated when transmitted back through the tissue to the detector. As an example, if a portion of around 0.001 of the light transmitted towards the skin reaches the cavity comprising the free gases, another attenuation factor of 0.001 has to be applied to the light travelling back from the cavity to be detected by the detector arranged on the surface of the skin. Hence the observed light which reaches the detector is about a millionth of the light transmitted by the light source towards the skin.

In the disclosed examples, the light source is arranged to transmit light to the tissue with losses as low as possible and then detect the light at the surface of the skin. By arranging the light source internally for decreasing the attenuation factor of the light transmitted to the tissue for measuring the free gas in a cavity, the total attenuation factor may be reduced to about 0.001 which is about 1000 times larger than what was previously be achieved.

The disclosed devices, systems and methods utilize a member for introducing the light sources for injecting the light into the tissue, for example, a bronchoscope, a nasogastric feeding tube, endoscope, a tracheal tube, a colonoscope or similar introducing members.

The group of patients considered to be most relevant when it comes to applying GASMAS technology for monitoring free gases in cavities are premature new-born infants. These infants often experience respiratory complications, such as breathing difficulties and problems with the lung functioning. Premature new-borns are therefore often connected to a medical ventilator to assist them with moving air into and out of the lungs. When connected to a medical ventilator, a premature new-born infant is intubated by a tracheal tube, such as an endotracheal tube. In one example of the description it is described how a fibre optical arrangement for delivering light to a cavity, such as the lung, may be conducted in combination with a tracheal tube, such as an endotracheal tube while detection of transmitted light is made at the skin surface.

In another example of the description it is described how a fibre optical arrangement for delivering light to a cavity, such as the lung, may be conducted in combination with a nasogastric feeding tube inserted into the oesophagus while detection of transmitted light is made at the skin surface.

Additionally, in another example, the light from the optical fibre arrangement is distributed over a larger distance or area by a light diffusing material.

Additionally, and/or alternatively, the transmitted light is detected at the skin surface by one or a plurality of detectors positioned at the skin over the cavity such as the lung. The detectors may be configured to be arranged at the skin surface or other means, such as optical fibres, could be used to collect the light at the skin surface and direct the collected light to a detector. In one example, a plurality of detectors may be used in parallel or sequentially to detect gases or a distribution of gases, or gas concentrations in different parts of the bronchial tree of a patient.

In this way, the results of changes in the settings of the medical ventilator or medications may be directly observed, and the information from the observation may be used to optimize the treatment of the patient using a feed-back system.

In some examples, the detection is made frequency- and phase-sensitively. The light, such as laser light, from the light source may be wavelength modulated at a selected frequency, and synchronous intensity variations may be detected when the modulation is conducted around a gas absorption wavelength. When modulation is conducted close to a gas absorption wavelength, the intensity of the detected light will quickly change at small variations of the wavelength, as described in S. Svanberg, Gas in Scattering Media Absorption Spectroscopy—from Basic Studies to Biomedical Applications, Lasers and Photonics Reviews 7, 779 (2013), which is incorporated herein by reference.

Alternatively, in some examples, a skin area may be detected by an imaging sensor, such as a digital camera, with high intensity dynamic both at an absorbing wavelength and at a close non-absorbing wavelength. The two images may then be compared, for example by division or subtraction, whereby the areas affected by gases may be visualized.

The same technology as described above for cavities, such as lungs, may be applied to monitoring gases, gas distribution or gas concentration in other cavities, for example in the digestive system, such as in the intestines. Here the light may be injected using an optical fibre arrangement in combination with a channel in an endoscope, an endoscope for esophagogastroduodenoscopy, or colonoscope or other minimally invasive devices. Abnormal gas distribution in the intestines, such as parts of the digestive tract, may be seen, for example when diagnosing the serious illness, necrotizing enterocolitis (NEC).

When utilizing the GASMAS technology, the determination of a gas concentration may be affected by the path length in the tissue the light interacting with the gas in the cavity has to travel through. The path length in the tissue is unknown due to multiple scattering. Hence light travelling both longer and shorted distances through the tissue may be detected at the same time. Beer-Lambert's relation which is normally used when analysing gas gives that the intensity of the absorption signal is determined by the product of the gas concentration and the path length (see S. Svanberg, Atomic and Molecular Spectroscopy—Basic Aspects and Practical Applications, 4th Edition, Springer, Berlin, Heidelberg 2004, which is incorporated herein by reference). When the path length is known, which is the case when measuring in a non-scattering material, the gas concentration may be directly calculated.

When utilizing the GASMAS technology for measuring a gas concentration, the path length through the gas is unknown; this need to be accounted for when performing a gas concentration measurement. Different method may be used for handling the problems of an unknown path length, these are discussed in, for example L. Mei, G. Somesfalean and S. Svanberg, Pathlength Determination for Gas in Scattering Media Absorption Spectroscopy, Sensors 14, 3871 (2014), which is incorporated herein by reference.

One of the most exact methods is to use profile changes in an absorption spectrum of, for example a water vapour absorption line. The changes in the profile of the water vapour line are dependent on the oxygen concentration, see P. Lundin, L. Mei, S. Andersson-Engels and S. Svanberg, Laser Spectroscopic Gas Concentration Measurements in Situations with Unknown Optical Path Length Enabled by Absorption Line Shape Analysis, Appl. Phys. Lett. 103, 034105 (2013), which is incorporated herein by reference. This method requires a good signal to noise ratio since the influence of the oxygen on the water vapour line is weak.

Another option is to perform the GASMAS measurements both for the gas concentration to be determined and for water vapour. The water vapour concentration may be assumed to be saturated in tissue and wherein the concentration is determined by the temperature which is known, see A. L. Buck, Buck Research Manuals; Updated Equation from (1981), which is incorporated herein by reference. New Equation for Computing Vapor Pressure and Enhancement Factor. J. Appl. Meteorol. 20, 1527 (1996), which is incorporated herein by reference. Based on the measured water vapour signal the effective path length may be calculated. The obtained path length may be approximately the same as for the gas, such as oxygen, nitric oxide (NO), or carbon dioxide, with an unknown concentration to be determined. The gas concentration, such as for oxygen, nitric oxide (NO), and carbon dioxide, may then be directly calculated using the approximated path length. This method works best when the light absorption and the light scattering in the tissue is the same for both measurements which is the case when the wavelengths used for the measurements are close. For example, oxygen is normally monitored around some of the sharp components in the oxygen molecule's A-band about 760 nm. Water vapour has a strong absorption around, for example 935 nm, but the difference in wavelength compared to oxygen may need to be corrected for due to differences in the optical properties at the different wavelengths. Therefore the weaker absorption wavelength for water vapour at around 820 nm may be a better choice.

One example of an implementation is illustrated in FIG. 1. The patient 1 in this example is a premature new-born baby. The new-born baby is connected to a medical ventilator 2 due to, under the circumstances common disorder, Respiratory distress syndrome (RDS).

The medical ventilator 2 is connected to the intubated patient 1 via, for example, an endotracheal tube 3 inserted in the trachea 4. In this example, two light sources 5, 6 are used for measuring a gas, for example oxygen at about 760 nm, and water vapour at about 820 nm. Depending on the measured gas other wavelengths may be used. In some examples other gases than water vapour may be used as a reference gas. The requirement is only that the gas concentration may be calculated without using the path length the detected light has travelled.

Alternatively, in other examples only one light source may be used. In some other examples more than two light sources may be used for detecting further gases, gas distributions or gas concentrations.

Alternatively other configurations of the light sources may be possible when using other methods related to GASMAS as previously described herein.

The light sources may be semiconductor lasers, for example distributed feed-back lasers (DFBL), vertical cavity surface emitting lasers (VCSEL) or other types of available lasers. The effect of the emitted light is preferably in the range 1 to 3000 mW.

The lasers may be driven by a current and temperature regulating unit included in the drive unit 7. The drive unit 7 may be controlled by a control unit 8, such as a computer. The control unit 8 may be used for signal processing and evaluation of the measured data.

Additionally, in some examples, the control unit 8 may be connected to the controller 9 of the medical ventilator 2 for controlling the settings of the medical ventilator 2. Additionally and/or alternatively, the controller 9 may also be used to control the distribution of medicaments 10 to the patient 1.

Additionally, in some examples, the lasers may be wavelength modulated by modulating the drive current on two separate frequencies. The frequencies may typically be in the region around 10 kHz to allow noise reduced phase-sensitive detection (lock-in-detection).

By using separated modulation frequencies, different gases, such as oxygen, nitric oxide (NO), and carbon dioxide, and water vapour, may be separated even though the light injection may be carried out through the same fibre 11. Light from individual optical fibres 12 connected to the light sources, such as the semiconductor lasers 5, 6, may be connected to a single injection fibre 11.

Additionally, in some examples, a small portion of the light to be injected may be diverted optically, such as by a fibre, to a calibration unit 13. The calibration unit 13 may be a gas cell including a gas to be detected, such as oxygen, nitric oxide (NO), and carbon dioxide. The gas has a known concentration and the gas cell has a predetermined length. The calibration unit 13 may also include a droplet of water and a temperature measuring unit. All parts of the calibration unit 13 may have a common detector unit.

Alternatively, in some examples, a compact diffuse multi-pass cell made from a porous material, such as ceramic may be used. The porous material may be enclosed in a compact gas cell, see T. Svensson, E. Adolfsson, M. Lewander, C. T. Xu and S. Svanberg, Disordered, Strongly Scattering Porous Materials as Miniature Multi-pass Gas Cells, Phys. Rev. Lett. 107, 143901 (2011), which is incorporated herein by reference.

The main part of the individually frequency marked light is led through optical fibre 11 down through the, in this example used, endotracheal tube 3.

Figure 2A:
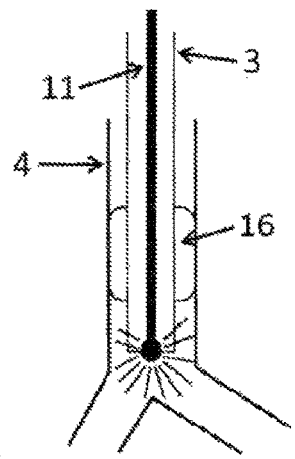
FIGS. 2A, 2B, 2C, and 2D are illustrating examples of arrangements of a light source in the trachea for measuring lung functions.
Figure 2B:
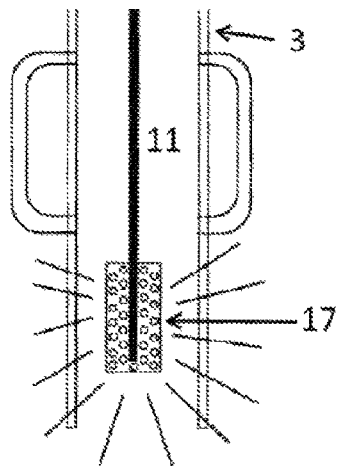
Figure 2C:
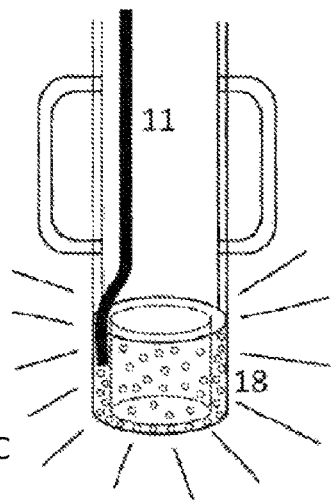
Figure 2D:
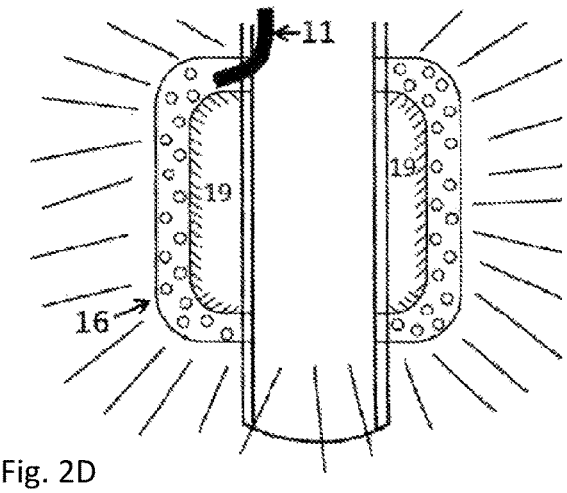

In the example illustrated in FIG. 2B to 2D the fibre 11 ends with a diffusor. The diffusor may be a structure on the surface of the fibre or a separate part made from a light scattering material. The diffusor is used to have the light distributed over a larger surface to reach a decreased surface power. A lower surface power may help to avoid raise in temperature of the tissue. Another advantage is eye safety if tests are performed outside the human body.

In some examples the injected light transmitted from the end of the end of the optical fibre 11, such as through the diffusor, may be transmitted to the tissue without passing any air in the trachea. If the light passes through air, the air may give some background signal in light detected by the detectors 14.

In one example, an inflatable cuff or balloon made from optically scattering material and with reflecting material on the inner walls may be used to have as much light as possible to be directly transmitted into the tissue, as seen in FIG. 2A.

Figure 3:
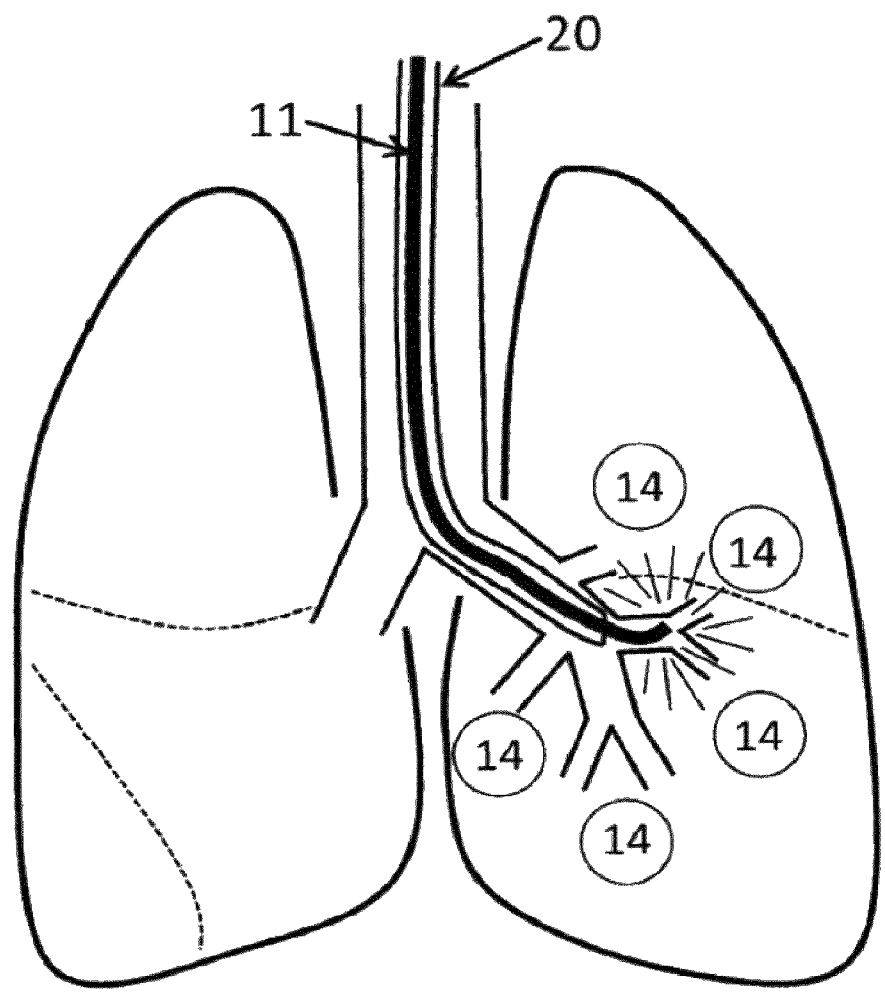
FIG. 3 is illustrating a further example of an arrangement of a light source using a bronchoscope for measuring lung functions.

The example illustrated in FIG. 2A gives good positioning of the optical fibre for monitoring the upper part of the lungs. By using a bronchoscope and a diffusing fibre end the light injection may be made deeper into the bronchial tree as illustrated in FIG. 3.

Alternatively and/or additionally, in some examples more than one, such as at least two, positions are used for light injection. When using more than one location for measuring, the measurements for the different locations need to be performed sequentially. Alternatively, more than one controllable standard fibre may be used.

When using more than one location for light injection and to obtain a better three-dimensional gas distribution analysis, diffuse light tomography may be used, as described in the articles J. Swartling, J. Axelsson, S. Svanberg, S. Andersson-Engels, K. Svanberg, G. Ahlgren, K. M. Kalkner and S. Nilsson, System for Interstitial Photodynamic Therapy with On-line Dosimetry—First Clinical Experiences of Prostate Cancer, J. Biomed. Optics 058003 (2010), which is incorporated herein by reference; and T. Durduran, R. Choe, W. B. Baker and A. G. Yodh, Diffuse Optics for Tissue Monitoring and Tomography, Rep. Progr. Phys. 73, 076701 (2010), which is incorporated herein by reference.

The detector or detectors 14 is/are adapted to be arranged against the skin. The detector should have a surface sized to detect the light transmitted through the tissue, for example in the range 0.25 to 5 $cm^2$, such as 1 $cm^2$. The detector may be made from different materials, such as germanium.

The detected light is transmitted as an electrical signal to the control unit 8. The signal may be evaluated using digital lock-in technology sequentially or in parallel, as described in the article L. Mei, and S. Svanberg, Wavelength Modulation Spectroscopy—Digital detection of Gas Absorption Harmonics based on Fourier Analysis, Applied Optics 54, 2254 (2015), which is incorporated herein by reference.

Alternatively, in some examples an analogue lock-in-amplifier may be used. The analogue lock-in-amplifier may be connected to the control unit 8.

Additionally, in some example threshold values may be selected. When the measured value has reached or passed the selected threshold values an alarm 15 may be activated for the health care personnel. The alarm 15 may be an acoustic alarm or an electronic alarm to a surveillance center.

FIGS. 2A to 2D are illustrating different examples of how to utilize a tracheal tube, such as an endotracheal tube.

FIG. 3 is illustrating an example wherein diffused light is injected using a working channel of a bronchoscope.

It may be observed that the same equipment, with some modification, may be used for external injection of light into the human body in those cases wherein a medical ventilator with a tracheal tube, or a bronchoscope is not used, for example through a feeding tube through the oesophagus. In these cases the light may be expanded and made diffused by a scattering medium with a large enough surface, for example a few $cm^2$, made in contact with the skin. This arrangement makes it possible to avoid local increase in tissue temperature, and eye safety is achieved.

FIG. 1 is illustrating an exemplary configuration of the disclosed device and system. Patient 1 is connected to a medical ventilator 2 via an introducing member 3, such as a bronchoscope, a tracheal tube, or an endotracheal tube, connected to the trachea 4.

In some other examples the introducing member 3 may be, for example, a nasogastric feeding tube.

The light sources 5, 6, such as lasers, with wavelength associated to the free gas of interest, for example, oxygen, nitric oxide (NO), and carbon dioxide, and a reference gas, for example water vapour.

In some examples other gases than water vapour may be used as a reference gas. The requirement is only that the gas concentration may be calculated without using the path length the detected light has travelled.

Alternatively, in other examples only one light source may be used. In some other examples more than two light sources may be used for detecting further gases, gas distributions or gas concentrations.

Alternatively other configurations of the light sources may be possible when using other methods related to GASMAS as previously described herein.

The light sources are connected to the drive unit 7, which is controlled by the control unit 8.

In some examples the measured value of the free gas in the lungs may be used for affecting the controller 9 for controlling the setting of the medical ventilator 2. Alternatively and/or additionally, in some examples, the measured value by the control unit 8 may be used to administration of a medicament 10.

The light it emitted to the tissue via an optical fibre 11. Light from individual optical fibres 12 connected to the light sources 5, 6, such as the semiconductor lasers, may be connected to a single fibre 11.

Additionally, in some examples, a small portion of the light to be injected may be diverted optically, such as by a fibre, to a calibration unit 13.

A detector 14 is configured to be positioned at a skin location at the chest of the patient for detecting the transmitted diffused light. The detected light carries information about the gas concentration in the lungs or gas distribution in the lung tissue, such as oxygen, nitric oxide (NO), and carbon dioxide concentration or distribution.

Additionally, in some examples, an alarm 15 may be activated when the measured value reaches or passes a selected threshold value.

FIGS. 2A to 2D are illustrating different examples of coupling the light form the optical fibre to the tissue for measuring lung functioning.

FIG. 2A is illustrating an example of a trachea tube 3, such as an endotracheal tube, with a balloon or cuff 16 being inflatable to prevent air leakage next to the trachea tube 3 which includes the optical fibre 11 for transmitting light down the trachea.

FIG. 2B is illustrating an example of an optical fibre 11 brought down a trachea tube, such as an endotracheal tube, to its end. At the end a light diffusor 17 is arranged as an ending to the optical fibre 11.

FIG. 2C is illustrating an example of how light in the fibre 11 may be connected to the end section 18 of a trachea tube, such as an endotracheal tube. The end section is made from a non-absorbing but strongly light scattering material.

FIG. 2D is illustrating an example of light from an optical fibre 11 may be coupled to a balloon or cuff 16. The balloon or cuff may be made from a non-absorbing but light scattering material. In some examples, the inner walls are coated 19 with a light reflecting material.

In an example, the laser light source is applied via the oesophagus rather than the trachea. In this example, the laser light source may be combined with the nasogastric feeding tube that is used in most infants in neonatal intensive care. The use of the nasogastric feeding tube for light application is advantageous because most infants already need to have such a device inserted, so no additional device needs to be introduced for the majority of patients. It is also advantageous since the oesophagus environment is less sensitive to infection, so the sterility requirements for the device could potentially be relaxed. It is also advantageous due to that the oesophagus is normally mostly collapsed, so there is potentially not a need for an expanding cuff to create good optical contact between the light source and the tissue. Further, lower parts of the lungs may also be more easily reached.

The light source should be positioned at a point in the oesophagus that represents a position close to the lungs. In an example, an optical fibre that guides the laser light is combined with the nasogastric feeding tube, so that the optical fibre goes along the tube to an adequate position along the tube. Nasogastric feeding tubes have marks that indicate how deep the tube is inserted, and these marks can be used to determine the position of the light source in the oesophagus.

In a preferred example, the optical fibre that guides the laser light is embedded in the tube wall during manufacturing of the nasogastric feeding tube, so that the nasogastric feeding tube and laser light guide comes as a single device.

In an example, the distal end of the optical fibre is terminated with a light diffusor that distributes the light over a larger area than would be provided by the fibre tip only. In a preferred example, when the optical fibre is embedded in the tube wall as described above, the diffusor is implemented by designing the tube wall in front of the fibre tip with light scattering properties so that the light scatters over an area along the tube corresponding to the desired characteristics of the diffusor. In an alternative example, the diffusor is manufactured as a separate component that is embedded in the tube wall similarly to the optical fibre.

In an example, alternatively, the diffusor can be made part of an expandable cuff similar to the diffusor described in connection with the trachea herein above.

The optical fibre may also be positioned in the nasogastric tube in such a way, that it may be sequentially moved to different positions along the tube for facilitating, e.g. a full tomographic view of the gas distribution, such as oxygen, nitric oxide (NO), and carbon dioxide distribution, using multiple detectors 14.

Alternatively, a plurality of optical fibres may be used in parallel at different positions for facilitating, e.g. a full tomographic view of the gas distribution, such as oxygen, nitric oxide (NO), and carbon dioxide distribution, using multiple detectors 14.

In alternative examples, the light source on the nasogastric feeding tube is implemented by placing one or multiple laser diodes directly at the site where the light source should be, and having electrical wires for driving the laser diodes along the nasogastric feeding tube. This implementation may also be applied to the cases of a tracheal tube.

Figure 4A:
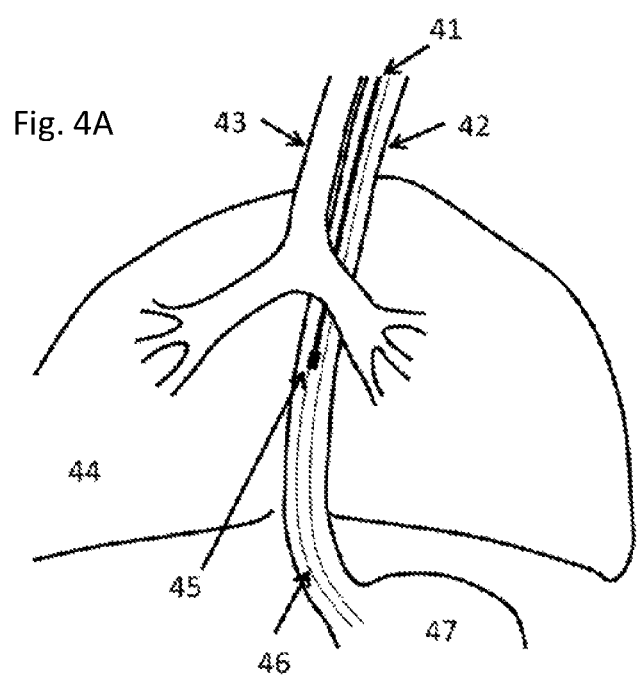
FIGS. 4A and 4B are illustrating further examples of an arrangement wherein a light source is inserted through the oesophagus.

FIG. 4A illustrates an optical fibre 41 combined with a nasogastric feeding tube 46 inserted into the oesophagus 42. The relation with the trachea 43 and the lungs 44 is also shown. At the distal end of the optical fibre 41, there may be a light diffusor 45. The upper part of the stomach 47 is also shown.

Figure 4B:
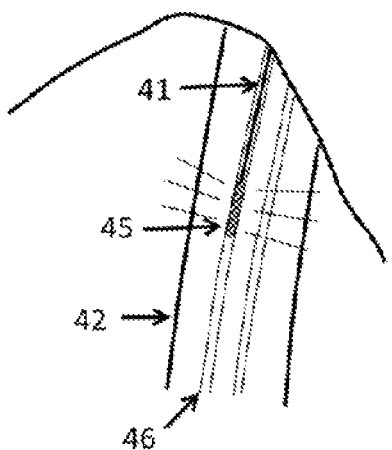

FIG. 4B illustrates a close-up of the optical fibre 41, embedded into the tube wall of the nasogastric feeding tube 46. The nasogastric feeding tube is inserted in the oesophagus 42. In this example, the optical fibre has a diffusor 45 at the distal end of the optical fibre 41. In other examples the optical fibre 41 may not have a diffusor.

The same examples of implementations described in relation to introducing the optical fibre for measuring free gases in a cavity using the trachea and the oesophagus are also applicable when using, for example, an endoscope or a colonoscope for evaluating abnormal gas distributions or gas concentrations in the intestines, or the digestive tract. In these cases the detector may be adapted to be positioned on the abdomen of the subject.

The present invention has been described above with reference to specific examples. However, other examples than the above described are equally possible within the scope of the disclosure. Different method steps than those described above, performing the method by hardware or software, may be provided within the scope of the invention. The different features and steps of the invention may be combined in other combinations than those described.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

The invention claimed is:

1. A system for determining a lung function of a subject, the system comprising:
   a light source configured for externally emitting light with a wavelength into the subject at more than one location and wherein the light source comprises a diffusor, and wherein the wavelength is associated with an absorption band of a free gas in a lung of the subject;
   a plurality of detector units adapted to be positioned on a skin surface for detecting light transmitted through tissue and a cavity of the lung; and
   a control unit for evaluating the detected light for determining functioning of the lung of the subject.

2. The system of claim 1, wherein the light source is a laser.

3. The system of claim 1, further comprising at least two light sources having different wavelengths.

4. The system of claim 3, wherein at least one light source has a wavelength associated with an absorption band of a reference gas.

5. The system of claim 4, wherein the reference gas is water vapour.

6. The system of claim 1, wherein the free gas is a physiological gas or a mixture of gases.

7. The system of claim 6, wherein the physiological gas comprises at least one gas selected from the group consisting of oxygen, nitric oxide, carbon dioxide, and water vapour.

8. The system of claim 1, wherein the control unit is configured for controlling a medical ventilator based on the distribution of the free gas, or the concentration of the free gas.

9. The system of claim 1, wherein the control unit is configured for controlling an administration of a medicament based on the distribution of the free gas, or the concentration of the free gas.

10. The system of claim 1, wherein the control unit is configured for activating an alarm when the determined free gas, the distribution of the free gas, or the concentration of the free gas reaches or passes a selected threshold value.

11. The system of claim 10, wherein evaluation is obtained as a three-dimensional gas distribution.

12. The system of claim 1, wherein the plurality of detector units comprise at least one imaging sensor, an absorbing wavelength and a close non-absorbing wavelength are sequentially emittable by the light source sequentially, two images are detectable by the plurality of image sensors, and detected two images are comparable by the control unit.

13. The device of claim 1, wherein line profile changes are evaluatable in an absorption spectrum by the control unit for determining the distribution of the free gas, or the concentration of the free gas.

* * * * *